United States Patent
Monteleone et al.

(10) Patent No.: US 6,488,924 B1
(45) Date of Patent: Dec. 3, 2002

(54) VITAMIN K ADDUCT, PARTICULARLY SUITABLE AS VITAMIN SUPPLEMENT FOR FEEDS

(75) Inventors: Francesco Monteleone, Cassina De'Pecchi (IT); Stefano Bonati, Milan (IT)

(73) Assignee: Luigi Stoppani S.p.A., Milan (IT)

( * ) Notice: Subject to any disclaimer, the term of this patent is extended or adjusted under 35 U.S.C. 154(b) by 0 days.

(21) Appl. No.: 09/592,558

(22) Filed: Jun. 12, 2000

(30) Foreign Application Priority Data

Jun. 17, 1999 (IT) ......................... MI99A1356

(51) Int. Cl.⁷ ..................... A61K 31/74; A61K 31/14
(52) U.S. Cl. ...................... 424/78.1; 514/643
(58) Field of Search ................... 424/78.1; 514/643

(56) References Cited

U.S. PATENT DOCUMENTS 3,196,010 A    7/1965  Galler
3,196,018 A  * 7/1965  Galler

FOREIGN PATENT DOCUMENTS

EP    0 281 204   9/1988
EP    0 435 684   7/1991

OTHER PUBLICATIONS

Huang et al., "Flow–injection determination of vitamin K3 by chemiluminescence sensor," Anal. Sci (1999) 15(12), 1227–1230.*

Dai et al., Studies on HPLC determination of vitamin K3 sodium bisulfite (menadione sodium sulfite) in premix and complete feed.*

Database WPI section Ch, week 199219 Derwent Publications Ltd., London, GB; An 1992–157335 XP002151111–& JP 04 099758 A (Nippon Shokubai Co Ltd), Mar. 31, 1992 abstract.

Chemical Abstract, vol. 112, No. 16, Apr. 16, 1990 Columbus, Ohio, US; abstract No. 140393m, Yan, Jun et al:"Adsorption behaviour of highly crosslinked–styrene–divinylbenzene copolymerz" p. 40; column 1; XP002151110 Abstract & Lizi Jiaohuan Yu Xifu, vol. 5, No. 3, 1989, pp. 186–191.

* cited by examiner

Primary Examiner—Thurman K. Page
Assistant Examiner—Blessing Fubara
(74) Attorney, Agent, or Firm—Guido Modiano; Albert Josif; Daniel O'Byrne

(57) ABSTRACT

A vitamin K adduct, particularly suitable as vitamin supplement for feeds, constitued by menadione bisulfite bonded with an appropriate ion-exchange resin and exceptionally stabilized thereby. The adduct can be used as an antihemorrhagic additive for farm animal feeds. The high thermal stability of the vitamin adduct allows to use it in modern technologies for producing feeds in extruded form.

17 Claims, No Drawings

VITAMIN K ADDUCT, PARTICULARLY SUITABLE AS VITAMIN SUPPLEMENT FOR FEEDS

BACKGROUND OF THE INVENTION

The present invention relates to a vitamin K adduct, particularly suitable as a vitamin supplement for feeds.

In particular, the present invention relates to a highly stable form of vitamin K, to its production process and to its use as vitamin supplement for feeds for farm animals.

Menadione (2-methyl-1,4-naphthoquinone) is a vitamin derivative ($K_3$) in the form of a yellow crystalline powder which is poorly soluble in water and has a high antihemorrhagic activity.

This substance intervenes in the biosynthesis of several factors involved in coagulation processes and therefore has long had specific applications both in the medical field and in the veterinary field.

However, use of this substance has been limited due to the discovery of application drawbacks, mainly linked to its limited stability to light, humidity, heat and pressure.

U.S. Pat. No. 2,367,302 also discloses another vitamin K adduct, menadione sodium bisulfite, known as MSB, which also has a high antihemorrhagic activity.

This adduct in salt form, having high solubility in water, has found specific use as vitamin additive for farm animal feeds.

Menadione sodium bisulfite also has limited stability to light, heat, humidity and pressure, particularly at ambient pH values above neutrality. Moreover, it has been found that in the presence of mineral salts and of some additives, such as choline chloride, commonly used in the formulas of feeds, it tends to decompose into an inactive form.

This phenomenon is even more evident at pH values below neutrality, in which the molecule isomerizes into a product which is poorly effective from the point of view of antihemorrhagic activity. This isomerization reaction becomes more conspicuous as the pH of the medium increases, until it becomes complete for a value of approximately 8.5.

In order to obviate these drawbacks, other forms of vitamin K have been synthesized, such as the ones disclosed in U.S. Pat. No. 3,328,169 (menadione dimethylpyrimidinol bisulfite MPB) and in Italian patent 1,097,391.

In particular, the latter patent, in the name of this same Applicant, discloses a menadione bisulfite salt with nicotinamide having low solubility in water and higher stability than MSB.

Though constituting an evolution in the formulation of vitamin compounds having an antihemorrhagic action, the stability characteristics of these last derivatives of vitamin K are not sufficiently adequate to allow their effective use in extrusion processes for feed production. In fact it has been found that these compounds tend to become inactive in the high temperature and humidity conditions typical of modern processes for the production of feeds in pellet form.

Moreover, their high rate of solubilization in water prevents their effective use as vitamin additives for fish feed formulas.

In the current situation, therefore, the need is felt to have new formulas of vitamin K available whose intrinsic characteristics allow to use them in modern extrusion plants for feed production.

SUMMARY OF THE INVENTION

A general aim of the present invention is to eliminate or lessen the drawbacks suffered in the above described known art.

An object of the present invention is to provide a vitamin K adduct having high thermal and pressure stability characteristics which allow its use in feed production processes which use modern extrusion technologies.

Another object of the present invention is to provide a vitamin K adduct which is substantially insoluble in water and in organic solvents commonly used in processes for the production of farm animal feeds.

Another object of the present invention is to provide a method for producing a menadione bisulfite derivative which can be produced easily with low production costs and with reduced environmental impact.

Another object of the present invention is to provide a vitamin K adduct with slow release of the active principle and whose elective use is as fish feed additive.

Within this aim, these and other objects which will become better apparent hereinafter, according to a first aspect of the present invention, a vitamin K adduct is provided which is particularly suitable as vitamin supplement for feeds and is characterized in that it comprises menadione bisulfite supported and stabilized on an ion-exchange resin.

The stabilization of said vitamin K adduct is particularly and surprisingly effective, since it can be partly ascribed to the formation of a chemical bond of menadione with the functional group of the resin and is partly determined by the inclusion of the menadione in the cavities of the polymeric matrix of said resin.

Within the scope of the present invention, the term "ion-exchange resin" designates a polymer with high relative molecular mass, preferably above $10^6$, which is substantially insoluble in water.

In particular, this definition includes strong basic anion exchange resins containing quaternary ammonium groups, weak basic resins containing primary, secondary, tertiary amine groups or mixtures thereof, and resins containing heterocyclic groups with one or more atoms of N, such as for example polyvinylpyridine and polyvinylpyrrolidone.

Particularly suitable ion-exchange resins are of the type with a styrene-divinylbenzene matrix containing quaternary ammonium groups, or resins of the type with an acrylic matrix containing ammonium groups.

DESCRIPTION OF THE PREFERRED EMBODIMENTS

In accordance with a preferred embodiment of the invention, said vitamin K adduct has the following structural formula:

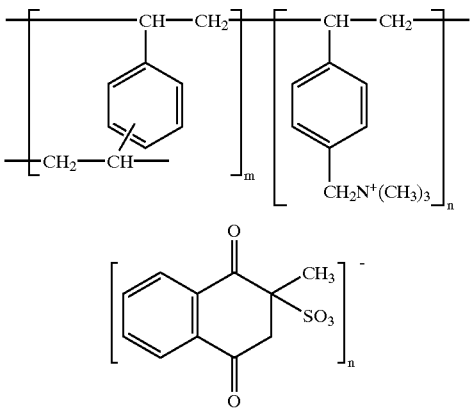

where n is a whole number greater than 1 and m is a whole number, preferably<n; said adduct being defined as 1,2,3,4- tetrahydro-2-methyl-1,4-dioxo-naphthalene sulfonate of trimethyl benzyl ammonium polystyrene-divinylbenzene copolymer.

The vitamin K adduct according to the preferred embodiment of the invention is further characterized by the following parameters:

| | |
|---|---|
| relative molecular mass: | higher than $10^6$ |
| melting point: | higher than 300° C. |
| solubility: | substantially insoluble in water and main organic solvents |
| menadione titer on the dry substance: | 1–55% |
| water | <2% |

It has been found that the vitamin K adduct according to the present invention has a high stability, which is determined by the presence of the polymeric structure of the resin as well as by the chemical bond with the functional group.

The polymeric matrix in fact embeds the menadione bisulfite molecule, fixing it firmly so as to make it difficult to split the ion bond of the polymer (resin) with the anion of vitamin $K_3$.

The presence of the resin thus gives it very high molecular stability to heat, pressure and humidity, further determining extremely low solubility in water.

These characteristics make the vitamin K formula according to the present invention suitable for applications which could not be hypothesized earlier.

The high stability characteristics of the adduct according to the invention allow its use, substantially without drawbacks, in processes for the production of feeds which use extrusion technologies.

It has also been found that the adduct according to the invention allows a gradual or delayed release of the active vitamin principle with antihemorrhagic activity, allowing its use as additive for fish feeds.

In general, the vitamin K adduct according to the invention is produced by ion-exchange reaction between a water-soluble derivative of menadione bisulfite and a strong or weak basic resin.

Suitable reagents are salts of menadione bisulfite, such as sodium, potassium or ammonium salts, strong basic resins, in the form of chloride or other anion, containing quaternary ammonium groups derived from trimethylamine, dimethylethanolamine or basic resins of the weak type containing primary, secondary, tertiary amine groups or mixtures thereof.

In accordance with another aspect of the present invention, a process for preparing a vitamin K adduct is therefore provided which comprises the steps of:

placing a menadione bisulfite solution in contact with an ion exchange resin in order to reach a high degree of saturation of the cation equivalents that are present;

washing with distilled water;

drying; and grinding in order to obtain a final product in the form of granules or powder.

The initial step of the process according to the invention can be provided by percolation of a solution of alkaline menadione bisulfite on a resin bed, up to saturation of the cationic equivalents that are present, or by immersion of the resin in a solution of alkaline menadione bisulfite, preferably in rising concentrations, in countercurrent, up to saturation of the cationic equivalents that are present.

An alternative method comprises the treatment of menadione (2-methyl-1,4-naphthoquinone) with a saturated solution of sodium metabisulfite until complete dissolution of the menadione is achieved, consequently forming menadione sodium bisulfite, followed by treatment with the resin according to the above described procedures.

The drying step is advantageously performed in a temperature range comprised from 40° to 120° C. and continues until a constant weight of the final product is achieved.

In accordance with a preferred embodiment, the resin used is of the styrene-divinylbenzene type which contains quaternary ammonium groups with a high content of meq per gram of dry substance (4–4.5 meq per g of dry substance).

Some comparative tests between the adduct according to the invention and the compound of the known art, menadione sodium bisulfite (MSB), are listed hereinafter.

| | Adduct according to the invention | MSB |
|---|---|---|
| Appearance: | free flowing beige powder | crystalline powder |
| water solubility: | insoluble | 50 g/100 ml at 25° C. |
| m.p.: | higher than 300° C. | Decomposes at 121–4° C. |
| Menadione titer: | 1–50% (on dry substance) | 51.5% min |
| Water: | less than 2% | cryst. $H_2O$ 10–16% |

The following examples are given merely as illustration of the present invention and must not be understood as limiting its scope as defined by the appended claims.

EXAMPLE 1

Thermal stability

Thermal stability tests are performed in an air-circulation stove at 120° for 24 hours on the adduct according to the invention and on MSB, in the absence of humidity:

TABLE 1

| | Adduct according to the invention | MSB |
|---|---|---|
| Men found/initial Men | 100% | 0% |
| Color | unchanged | Purple |

EXAMPLE 2

Thermal Stability in Controlled Humidity

A method described in the literature is used to compare the stability of Kavist with respect to MSB. According to this method, the products, as accurately dispersed in aluminum silicate (K.F. humidity around 11%) at the level of 1.5% by weight, are kept at 55° C. for 3 days in order to evaluate their menadione content before and after the treatment. The menadione titers of the adduct according to the invention and the percentage of menadione left unchanged before and after the treatment are listed hereafter.

TABLE 2

| | Adduct according to the invention | MSB |
|---|---|---|
| Initial menadione content | 1.46% | 1.52% |
| Final menadione content | 1.46% | 0.24% |
| Final menadione/initial menadione | 100% | 15.5% |

EXAMPLE 3

Stability Under Pressure

The effect of high pressure combined with high temperatures on the adduct according to the invention is evaluated by way of the action of a press on a disk of finely ground powder for 30 minutes. Table 3 below lists the percentages of menadione left unchanged before and after the treatment on the adduct according to the invention and, by comparison, on MSB.

TABLE 3

|  | Adduct according to the invention | | | MSB | | |
|---|---|---|---|---|---|---|
| Pressure | 1 atm | 25 atm | 5000 atm | 1 atm | 25 atm | 5000 atm |
| temp. 25° C. | 100% | 100% | 100% | 100% | 100% | 80% |
| temp. 120° C. | 100% | 100% | 100% | 20% | 15% | 10% |

EXAMPLE 4

Solubility in Water

The adduct according to the invention is subjected to solubility tests at ambient temperature in demineralized water (saturated solution in presence of a precipitate). The concentration of menadione in the solution is found to be very low, as shown by the table that follows; comparison with MSB shows that the release of menadione in the aqueous solution is several orders of magnitude smaller.

TABLE 4

|  | Adduct according to the invention | MSB |
|---|---|---|
| Menadione concentration mg/l saturated solution | less than 10 mg | Higher than $20 \times 10^4$ mg |

EXAMPLE 5

Release of Menadione in Aqueous Medium

The menadione release capacity of the adduct according to the invention and of MSB in three different types of water (demineralized water, municipal drinking water, and seawater) is evaluated. MSB exhibits substantially instantaneous release which follows the solubility of the compound in water; for the adduct according to the invention, release is in any case slow and depends on the salinity of the medium.

The following table lists the milligrams/liter of menadione found in the solution with respect to the total menadione of the polymeric adduct added as a suspension equal to 1 g/l (360 g menadione on 1 g of dry adduct):

TABLE 5

|  | Demineralized water | Drinking water | Seawater |
|---|---|---|---|
| Menadione in solution after 4 hours (mg) | 6.5 | 113 | 318 |
| % on initial menadione | 1.8 | 31.4 | 88.4 |

EXAMPLE 6

Bioavailability tests are then conducted by adopting the following method, which simulates the conditions of the gastrointestinal system of a chicken:

A weighed amount of adduct, corresponding to 25 mg of menadione, is subjected to treatment under agitation, at the temperature of 41° C., in 100 ml of a solution of HCl and pepsin with a pH of 2.2. After 30 minutes, the mixture is brought to pH 5.8 with $NaHCO_3$. Pancreatin is added and agitation is continued at the same temperature for another 20 minutes.

The percentage of menadione recovered in the solution, with respect to the menadione contained in the adduct, directly expresses bioavailability:

|  | Adduct | MSB |
|---|---|---|
| Recovered menadione (bioavailability) | 93% | 92% |

EXAMPLE 7

Preparation 10.0 g of a strongly basic ion-exchange resin in pelletized moist chloride form are introduced in a glass column provided with a porous partition, taking care to achieve good packing. 250 ml of an aqueous solution of MSB (approximately 0.70 M) at ambient pressure and temperature are percolated through the resin with a flow rate of approximately 7 ml per minute. Then the resin is washed, allowing percolation of another 100 ml of water through it. The resulting pelletized moist product is dried at 120° C. and ground. In this manner, 7.0 g of adduct with a 40.4% menadione titer are obtained.

EXAMPLE 8

10.0 g of a ground and dry strongly basic ion-exchange resin are kept under agitation at ambient temperature for 1 hour in a solution of 0.6 M of MSB. The suspension is filtered and the cake is washed with 50 ml of water; the moist product is resuspended in a solution identical to the solution of the first pass and agitation is performed for 1 hour. The operation is repeated at least once more, checking for the presence of chlorides in the stock solution. If the release of chlorides is complete, the product is washed with water and dried in a stove (120° C.). 17.7 g of dry adduct with a 35.0% menadione titer are obtained.

EXAMPLE 9

As in example 2, but the moist product recovered from each individual pass is suspended in the spent MSB solution at rising concentration deriving from the preceding exchange (countercurrent).

EXAMPLE 10

48.0 g of menadione are added to 250 ml of a 2 M solution of $NaHSO_3$, keeping the temperature at 30° C. The result is a solution which can be used as a source of MSB in one of examples 1, 2 or 3.

EXAMPLE 11

250 ml of a solution of 0.7 M of MSB are exchanged with an appropriate cation-exchange resin which is strongly acid in H form. The result is a solution of the sulfonic acid that corresponds to the MSB. This solution is immediately placed in contact with 10 g of a weak basic ion-exchange resin such as styrene-polyamide in the manner described in example 1. The dried and ground resulting product has a minimum menadione titer of 22%.

EXAMPLE 12

Stability in extruded feed

Three forms of vitamin K supplement, menadione sodium bisulfite, menadione nicotinamide bisulfite and the vitamin K adduct according to the invention, were added in an amount of approximately 100 mg menadione/kg to a complete formula of feed for a fish farm.

Two preparations of vitamin supplement of approximately 2500 kg of feed were prepared for each vitamin K source. The vitamin K supplements were mixed in with the feed in an industrial mixer, extruded in a continuous extruder with the addition of live steam, dried and added with fat.

The preparations were sampled after mixing, in order to check and confirm the level of approximately 100 mg/kg and at the end of the process, after the addition of fat.

| Sampling point | MSB | | MNB | | Adduct according to the invention | |
|---|---|---|---|---|---|---|
| | 1st | 2nd | 1st | 2nd | 1st | 2nd |
| Mixer (mg/kg) | 90.9 | 87.6 | 86.1 | 86.3 | 90.6 | 92.6 |
| End point (mg/kg) | 21.0 | 16.1 | 22.7 | 18.1 | 34.2 | 35.4 |

The disclosures in Italian Patent Application No. MI99A001356 from which this application claims priority are incorporated herein by reference.

What is claimed is:

1. A vitamin K adduct, comprising a menadione bisulfite bonded with an ion-exchange resin.

2. The vitamin K adduct according to claim 1, wherein said ion-exchange resin is a polymer with high relative molecular mass which is insoluble in water.

3. The adduct according to claim 1, wherein said resin is the group consisting of strong basic resin containing quaternary ammonium groups, weak basic resin containing primary, secondary, tertiary amine groups and resin containing a heterocyclic group with one or more nitrogen atoms.

4. The adduct according to claim 1, wherein said resin is a resin with a styrene-divinylbenzene matrix containing quaternary ammonium groups.

5. The adduct according to claim 4, wherein said resin is a strongly basic macroreticular anion-exchange resin containing $-N^+(CH3)_3$ at the level of approximately 4 meq/g of dry resin.

6. The adduct according to claim 1, wherein said adduct has the following structural formula:

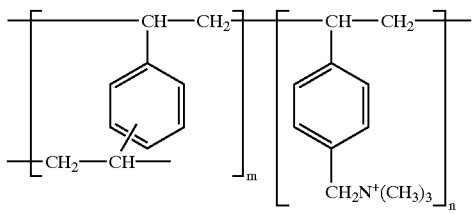

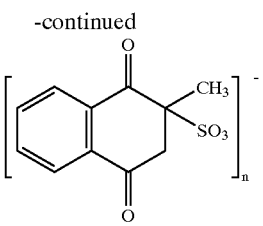

where n is a whole number>1 and m is a whole number<n.

7. A method for treating hemorrhage in fish comprising the administration of a vitamin K adduct comprising it. menadione bisulfite bonded with an ion-exchange resin.

8. Method according to claim 7, wherein said additive is in the form of extruded or pelletized feeds.

9. A feed in extruded form, comprising a vitamin K adduct comprising a menadione bisulfite bonded with an ionexchange resin.

10. A method for producing a vitamin K adduct, comprising an ion-exchange reaction between a water-soluble compound of menadione bisulfite and an anion-exchange resin.

11. The method according to claim 10, wherein said menadione bisulfite compound is in acid or salt form.

12. The method according to claim 10, wherein said ion-exchange resin is selected from the group consisting of strong basic resins, in the form of Cl or other anion, containing quaternary ammonium groups derived from trimethylamine, dimethylethanolamine and weak basic resins containing primary, secondary, tertiary amine groups or mixtures thereof.

13. The method according to claim 10, comprising the steps of:
placing a solution of menadione bisulfite in contact with an ion-exchange resin in order to reach a high degree of saturation of the cationic equivalents that are present;
washing with distilled water;
drying; and
grinding in order to obtain a final product in the form of granules or powder.

14. The method according to claim 13, wherein the step of placing a solution of menadione bisulfite in contact with the ion.exchange resin is made by percolation of a solution of alkaline menadione bisulfite on a resin bed up to saturation of the cationic equivalents that are present.

15. The method according to claim 13, wherein the step of placing a solution of a menadione bisulfite in contact with the ion.exchange resin is made by immersion of the resin in a solution of alkaline menadione bisulfite in countercurrent up to saturation of the cationic equivalents that are present.

16. The method. according to claim 13, wherein said drying. step is performed at a temperature in the range between 40 and 120° C. and is extended until a constant weight of adduct is reached.

17. The method according to claim 14, wherein said resin is a styrene-divinylbenzene resin containing quaternary ammonium groups with a content of 4–4.5 meq per gram of dry resin.

* * * * *